(12) United States Patent
Squires et al.

(10) Patent No.: US 8,066,774 B2
(45) Date of Patent: Nov. 29, 2011

(54) ARTIFICIAL DISC IMPLANTS AND ASSOCIATED METHODS AND INSTRUMENTATION

(75) Inventors: Craig M. Squires, Cordova, TN (US); Greg C. Marik, Memphis, TN (US); William Cedrick McCormack, Corinth, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1170 days.

(21) Appl. No.: 11/400,657

(22) Filed: Apr. 7, 2006

(65) Prior Publication Data
US 2007/0239276 A1 Oct. 11, 2007

(51) Int. Cl.
*A61F 2/44* (2006.01)

(52) U.S. Cl. ........... 623/17.16; 623/17.14; 623/17.15

(58) Field of Classification Search .... 623/17.11–17.16, 623/19.12, 20.14
See application file for complete search history.

(56) References Cited

U.S. PATENT DOCUMENTS

| | | |
|---|---|---|
| 572,486 A | 12/1896 | Horn |
| 3,320,951 A | 5/1967 | Wittebol |
| 3,510,883 A | 5/1970 | Cathcart |
| 3,740,769 A | 6/1973 | Haboush |
| 3,903,549 A | 9/1975 | Deyerle |
| 4,205,400 A * | 6/1980 | Shen et al. ........... 623/17.11 |
| 4,309,777 A | 1/1982 | Patil |
| 4,470,158 A | 9/1984 | Pappas et al. |
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,743,262 A | 5/1988 | Tronzo |
| 4,759,766 A | 7/1988 | Buettner-Janz et al. |
| 4,805,607 A | 2/1989 | Engelhardt et al. |
| 4,874,389 A | 10/1989 | Downey |
| 4,875,474 A | 10/1989 | Border |
| 4,892,545 A | 1/1990 | Day et al. |
| 4,932,975 A | 6/1990 | Main et al. |
| 4,936,363 A | 6/1990 | Schuster et al. |
| 4,946,378 A | 8/1990 | Hirayama et al. |
| 4,997,432 A | 3/1991 | Keller |
| 5,004,476 A | 4/1991 | Cook |
| 5,037,438 A | 8/1991 | Davidson |
| 5,062,850 A | 11/1991 | MacMillan et al. |

(Continued)

FOREIGN PATENT DOCUMENTS

CH  624573 A5  8/1981

(Continued)

OTHER PUBLICATIONS

Viscoglioski Bro., LLC, Spine Arthoplasty: Market Potential & Technology Update, Spine Industry Analysis Series, Nov. 2001, pp. 1-215.

(Continued)

*Primary Examiner* — Eduardo C Robert
*Assistant Examiner* — Jacqueline Johanas (57) ABSTRACT

An artificial disc implant and associate methods and instrumentation are provided for the artificial disc implant that includes opposite vertebral endplate members and a spacer member between the vertebral endplate members. An anchoring member extends from at least one of the vertebral endplate members toward an adjacent vertebral endplate when the implant is positioned between vertebrae. The anchoring member can be received in an anchor seat formed in the adjacent vertebral endplate without requiring the artificial disc implant to be impacted into the space between vertebrae to engage the anchoring member in the seat.

32 Claims, 8 Drawing Sheets

U.S. PATENT DOCUMENTS

| | | | |
|---|---|---|---|
| 5,071,437 A | 12/1991 | Steffee |
| 5,108,442 A | 4/1992 | Smith |
| 5,122,130 A | 6/1992 | Keller |
| 5,271,737 A | 12/1993 | Baldwin et al. |
| 5,282,868 A | 2/1994 | Bahler |
| 5,290,312 A | 3/1994 | Kojimoto et al. |
| 5,314,477 A | 5/1994 | Marnay |
| 5,344,458 A | 9/1994 | Bonutti |
| 5,425,773 A | 6/1995 | Boyd et al. |
| 5,507,816 A | 4/1996 | Bullivant |
| 5,509,934 A | 4/1996 | Cohen |
| 5,534,029 A | 7/1996 | Shima |
| 5,534,030 A | 7/1996 | Navarro et al. |
| 5,554,191 A | 9/1996 | Lahille et al. |
| 5,571,190 A | 11/1996 | Ulrich et al. |
| 5,591,235 A | 1/1997 | Kuslich |
| 5,609,638 A | 3/1997 | Price et al. |
| 5,658,347 A | 8/1997 | Sarkisian et al. |
| 5,676,701 A | 10/1997 | Yuan et al. |
| 5,683,465 A | 11/1997 | Shinn et al. |
| 5,702,469 A | 12/1997 | Whipple et al. |
| 5,755,811 A | 5/1998 | Tanamal et al. |
| 5,800,547 A | 9/1998 | Schafer et al. |
| 5,824,094 A | 10/1998 | Serhan et al. |
| 5,888,222 A | 3/1999 | Coates et al. |
| 5,899,941 A | 5/1999 | Nishijima et al. |
| 6,010,502 A | 1/2000 | Bagby |
| 6,096,080 A | 8/2000 | Nicholson et al. |
| 6,102,954 A | 8/2000 | Albrektsson et al. |
| 6,113,638 A | 9/2000 | Williams et al. |
| 6,251,140 B1 | 6/2001 | Marino et al. |
| 6,264,655 B1 | 7/2001 | Pisharodi |
| 6,325,827 B1 | 12/2001 | Lin |
| 6,368,350 B1 | 4/2002 | Erickson et al. |
| 6,368,353 B1 | 4/2002 | Arcand |
| 6,375,681 B1 | 4/2002 | Truscott |
| 6,402,785 B1 | 6/2002 | Zdeblick et al. |
| 6,413,278 B1 | 7/2002 | Marchosky |
| 6,641,614 B1 | 11/2003 | Wagner et al. |
| 6,740,118 B2 * | 5/2004 | Eisermann et al. | 623/17.14 |
| 6,780,186 B2 | 8/2004 | Errico et al. |
| 6,936,071 B1 | 8/2005 | Marnay et al. |
| 6,966,929 B2 | 11/2005 | Mitchell |
| 2002/0099444 A1 | 7/2002 | Boyd et al. |
| 2003/0045939 A1 | 3/2003 | Casutt |
| 2004/0143332 A1 | 7/2004 | Krueger et al. |
| 2004/0230307 A1 | 11/2004 | Eisermann |
| 2005/0055098 A1 * | 3/2005 | Zdeblick et al. | 623/17.11 |
| 2005/0119753 A1 | 6/2005 | McGahan et al. |
| 2005/0159818 A1 | 7/2005 | Blain |
| 2005/0261772 A1 * | 11/2005 | Filippi et al. | 623/17.13 |
| 2005/0283237 A1 * | 12/2005 | Zucherman et al. | 623/17.11 |

FOREIGN PATENT DOCUMENTS

| | | |
|---|---|---|
| DE | 2804936 | 2/1979 |
| DE | 3032353 C2 | 9/1981 |
| FR | 2724108 A1 | 2/1994 |
| FR | 2718635 A1 | 9/1995 |
| FR | 2742653 A1 | 12/1995 |
| JP | 2261446 | 10/1990 |
| WO | WO 03/059212 A1 | 7/2003 |
| WO | WO 2005/094736 A1 | 10/2005 |

OTHER PUBLICATIONS

Jeanette E. Ahrens, PHD, Alexis P. Shelokov, MD, Jeffrey L. Carver, BS, Normal Joint Mobility is Maintained with an Artifical Disc Prothesis, Texas Health Research Institute, Plano, Texas, HCA Columbia Hospital, Plano, Texas, Joint Biomedical Engineering Program, University of Texas Arlington, Link America, Inc., Denville NJ and Waldemar Link, Inc., Hamburg, Germany, 1999.

T. Hoogland, A. D. Steffe, J.D. Black, A.S. Greenwald, Cleveland Clinic Foundation, 24 Annual ORS Dallas, Texas, Feb. 21-23, 1978.

David S. Hungerford, M.D., Kenneth A. Krackow, M.D., Robert V. Kenna, Total Knee Arthoplasty: A Comprehensive Approach, Williams & Williams, Baltimore, MD., 1984, Chapter 5, pp. 71-88.

David S. Hungerford, M.D., and Robert V. Kenna, Preliminary Experience with a Total Knee Prothesis with Porous Coating Used Without Cement, J.B. Lippincott, Co., No. 176, Jun. 1983, pp. 95-107.

AB Swanson, GD Swanson, T Powers, MA Khalil, BK Maupin, DE Mayhew and SH Moss, The Journal of Bone & Joint Surgery: Unicompartmental and bicompartmental arthroplasty of the knee with a finned metal tibial-plateau implant, vol. 67-A, No. 8, Oct. 1995, pp. 1175-1182, The Journal of Bone & Joint Surgery, Jun. 1994.

The Journal of Bone and Joint Surgery, Sep. 1971, American Volume, vol. 53-A, No. 6, Zimmer, Warsaw, Indiana, U.S.A., Zimmer of Canada, Ltd.

The Journal of Bone and Joint Surgery, Jul. 1970, American Volume, vol. 52-A, No. 5, Zimmer, Warsaw, Indiana, U.S.A., Zimmer of Canada, Ltd.

A.H. Crenshaw, Cambell's Operative Orthopedics, Seventh Edition, vol. Two, The C.V. Mosby Company, copyright, 1987.

TH Marnay, L'Arthoplatie Intervertebral Lombaire, Orthopedic Sugeon, Kennedy Clinic, 30000 Nimes.

TH Marnay, English translation of "L'Arthoplatie intervertebral Lombaire.", Kennedy Clinic, 30000 Nimes.

Nobou, English translation of JP 2261446.

Grosse, English translation of FR 2742653.

* cited by examiner

ARTIFICIAL DISC IMPLANTS AND ASSOCIATED METHODS AND INSTRUMENTATION

FIELD OF THE INVENTION

The present invention relates generally to the field of intervertebral implants, and more particularly relates to artificial disc implants and associated methods and instrumentation.

BACKGROUND

With regard to spinal deformities, the intervertebral disc space can lose its functionality as a result of disease, trauma or other defect. Intervertebral implants have been developed to restore the natural height and functionality of the disc space. However, such implants can expel or move relative to the vertebral endplates after implantation, potentially resulting in suboptimal post-operative positioning in the disc space. In order to assist in maintaining the positioning of the implant in the disc space, implants have been provided with structures that engage the vertebral endplates adjacent the disc space and/or allow bone ingrowth into the implant while retaining desired motion capabilities of the implant. However, such structures can require impaction of the implant into the space between the vertebral endplates to secure the structures to the vertebrae. The impaction of the implant must be carefully controlled and monitored to prevent or avoid over-insertion and impingement on anatomical structures adjacent the disc space, such as the spinal canal.

Thus, there remains a need for improved intervertebral implants, surgical methods, and instrumentation that can facilitate positioning of the implant within the disc space and in engagement with at least one of the endplates without impaction of the implant into the disc space. The present invention satisfies these needs and provides other benefits and advantages in a novel and unobvious manner.

SUMMARY

The present invention relates generally to an artificial disc implant and associated methods and instrumentation. While the actual nature of the invention covered herein can only be determined with reference to the claims appended hereto, certain forms of the invention that are characteristic of the embodiments disclosed herein are described briefly as follows.

According one aspect, an artificial disc for implantation within an intervertebral disc space between adjacent vertebrae includes first and second endplate members coupled in movable relation to one another. The first and second endplate members can be sized and shaped for positioning in the intervertebral disc space to movably support the adjacent vertebrae. An anchoring member extends from an endplate contacting surface of the second endplate member in a direction opposite the first endplate member for engagement with the adjacent vertebra. The anchoring member includes a tapering configuration that can be seated in a correspondingly shaped seat in the adjacent vertebra to contact the bone of the vertebra and resist displacement of the implant relative to the vertebrae.

In another aspect, trial guide instruments and reamers are provided to facilitate preparation of the adjacent vertebrae to receive an artificial disc implant with an anchoring member. The trial guide instrument can include a bore to guide the reamer into at least one of the adjacent vertebra in an oblique orientation to the respective vertebral endplate to form a seat to receive the anchoring member of the implant.

Surgical methods for preparing adjacent vertebrae and for inserting artificial disc implants are also provided. The methods involve forming a seat in an endplate of at least one vertebra where the seat is obliquely oriented to the endplate of the vertebra. The methods may also include inserting an artificial disc implant into the disc space with an anchoring member received and engaged in an obliquely oriented seat formed in the vertebra.

It is one object of the present invention to provide an improved artificial disc implant and associated methods and instrumentation. Further objects, features, advantages, benefits, and aspects of the present invention will become apparent from the drawings and description contained herein.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Referring to FIGS. 1-4, shown therein is an artificial disc implant 20 according to one form of the present invention. The artificial disc implant 20 extends generally along a longitudinal axis L and includes a first vertebral endplate member 30, a second vertebral endplate member 50, and a spacer member 22 between endplate members 30, 50. Spacer member 22 can include any suitable form for extending between endplate members 30, 50 while allowing relative motion between the vertebrae to which endplate members 30, 50 are engaged. Spacer member 22 may be in the form of a ball member or include one or more hemispherical portions that provide a ball and socket type arrangement with one or both of endplate members 30, 50. Spacer member 22 may be integral with one of the endplate members 30, 50 or a separate component from each. In one embodiment, spacer member 22 includes a cylindrical-like body that is compressible and elastic to allow movement of the endplate members 30, 50 relative to one another when implanted between vertebrae. In a further embodiment, spacer member 22 can include a shell extending around a spring or cushioning type member or substance between endplate members 30, 50.

In the illustrated embodiment, spacer member 22 is a dome shaped member with opposite ends 24, 26 at least one of which can be rounded and positioned in correspondingly shaped recess in the respective endplate member 30, 50 to maintain spacer member 22 in engagement therewith. First endplate member 30 is shown in the Figures positioned above or superiorly to spacer member 22 and second endplate member 50 and in engagement with an upper or superior vertebra. It should be understood that first endplate member 30 could be positioned below spacer member 22 for engagement with a lower or inferiorly located vertebra.

Figure 1:
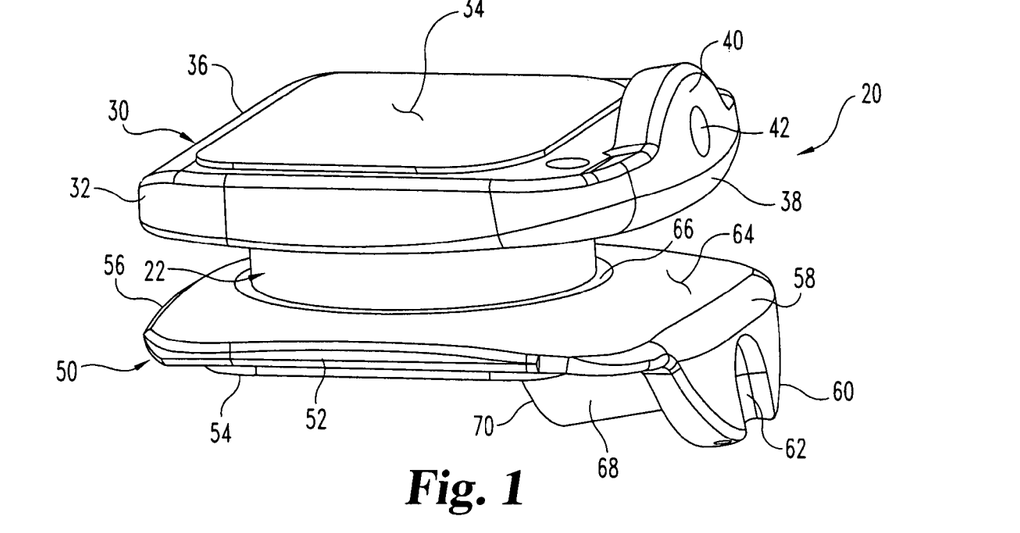
FIG. 1 is a perspective view of an artificial disc implant.
Figure 2:
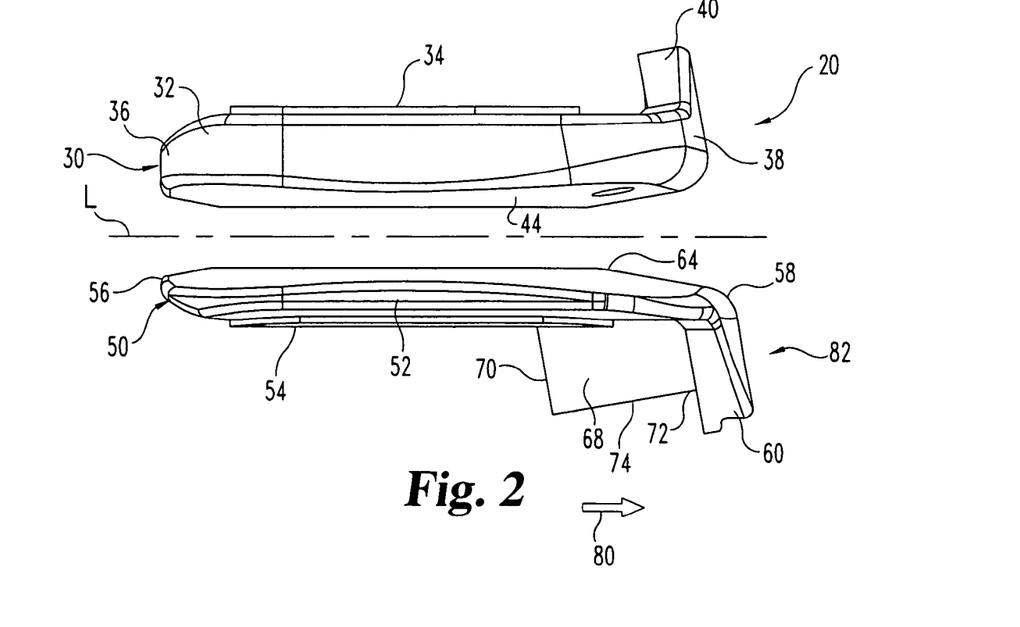
FIG. 2 is a side elevation view of the implant of FIG. 1 with a spacer member removed from between the opposite vertebral endplate members.
Figure 4:
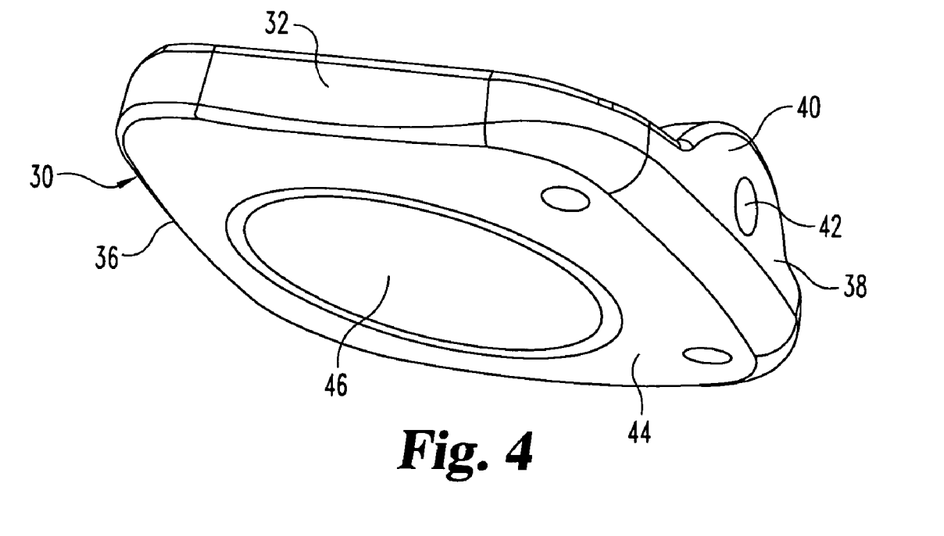
FIG. 4 is a perspective view looking toward the inner side of the other endplate member of the artificial disc implant of FIG. 1.

First endplate member 30 includes a body portion 32 positionable along an endplate of an adjacent vertebra. Body portion 32 further extends between a distal leading insertion end 36 and an opposite proximal trailing end 38. Leading insertion end 36 can be rounded and tapered distally to facilitate placement between vertebral bodies and into the disc space. Body portion 32 can be rectangular, square, oval, D-shaped, kidney shaped, or have any other suitable configuration. Body portion 32 includes an endplate contacting surface 34 located on an outer side thereof that is opposite spacer member 22. Endplate contacting surface 34 can be rectangular as shown, or include any other suitable shape that is similar to or that differs from the shape of body portion 32. Endplate contacting surface 34 can reside in a corresponding milled or prepared surface of the vertebral endplate. Endplate contacting surface 34 can include ridges, teeth, spikes, roughening, knurlings, pores or other structure to facilitate bone ingrowth and interlocking engagement with the adjacent vertebral endplate, although such is not required.

Trailing end 38 can include a stop member or flange 40 extending therefrom in a direction toward and projecting from endplate contacting surface 34. Flange 40 can include a bore 42 to receive a bone screw or other suitable bone anchor that engages the adjacent vertebral body. In the illustrated embodiment, flange 40 includes a rounded or dome shape along its outer perimeter to minimize its intrusiveness into adjacent tissue along the vertebra. Body portion 32 further includes an inner surface 44 oriented toward second endplate member 50. Inner surface 44 defines a receptacle 46 sized and shaped to receive a portion of spacer member 22 therein when artificial disc implant 20 is assembled. Receptacle 46 can be partially spherical to receive an adjacent dome-shaped end of spacer member 22 while allowing pivoting motion therebetween. Recess 46 can also include any other suitable shape to accommodate spacer member 22. In another embodiment, inner surface 44 includes a projection that engages a recess in the adjacent surface of spacer member 22.

Figure 3:
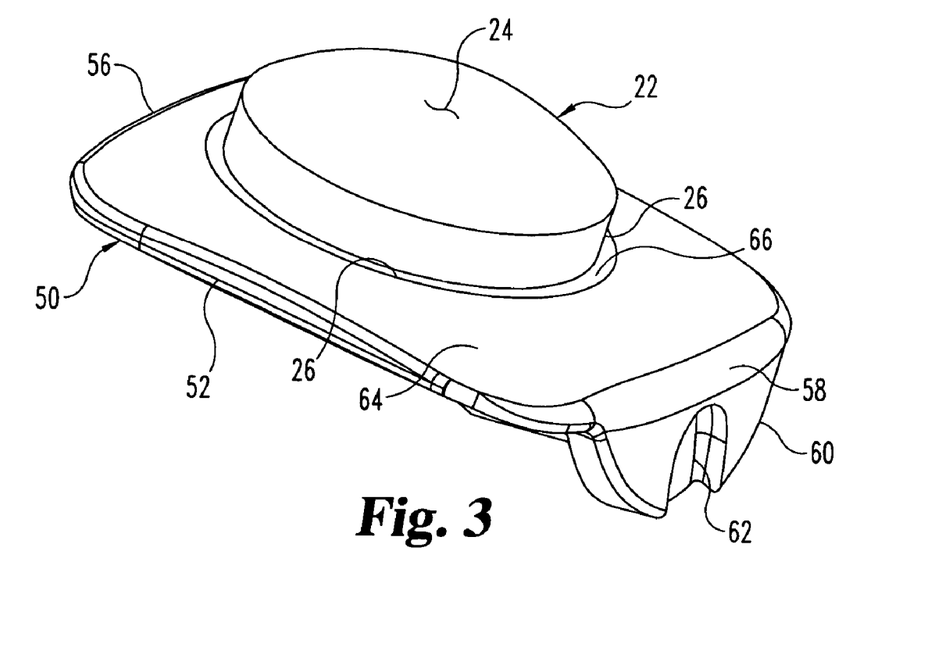
FIG. 3 is a perspective view looking toward a spacer member and an endplate member of the artificial disc implant of FIG. 1 with the other endplate member removed.

Second endplate member 50 includes a body portion 52 positionable along an endplate of an adjacent vertebra. Body portion 52 further extends between a distal leading insertion end 56 and an opposite proximal trailing end 58. Leading insertion end 56 can be rounded and tapered distally to facilitate placement between vertebral bodies and into the disc space. Body portion 52 can be rectangular, square, oval, D-shaped, kidney shaped, or have any other suitable configuration that is the same as or that differs from the shape of body portion 32. Body portion 52 includes an endplate contacting surface 54 located on an outer side thereof that is opposite spacer member 22. Endplate contacting surface 54 can be rectangular as shown, or include any other suitable shape that is similar to or that differs from the shape of body portion 52. Endplate contacting surface 54 can include ridges, roughening, teeth, spikes, knurlings, pores or other structure to facilitate bone ingrowth and interlocking engagement with the adjacent vertebral endplate, although such is not required.

Trailing end 58 can include a stop member or a flange 60 extending therefrom in a direction toward and projecting from endplate contacting surface 54. Flange 60 can include a solid groove 62 therein that opens proximally in the direction away from body portion 52. In the illustrated embodiment, flange 60 includes a rounded or dome shape around its perimeter to minimize its intrusiveness into adjacent tissue. Body portion 52 further includes an inner surface 64 oriented toward first endplate member 30. Inner surface 64 can define a receptacle 66 sized and shaped to receive a portion of spacer member 22 therein if spacer member 22 were provided separated from endplate member 50. Receptacle 66 can be partially spherical to receive an adjacent dome-shaped end of spacer member 22 while allowing pivoting motion therebetween. Recess 66 can also include any other suitable shape. It is also contemplated that spacer member 22 can be integrally formed with or irremovably attached to a respective one of the endplate members 30, 50.

Flange 60 abuts the adjacent vertebra and prevents or resists movement of artificial disc implant 20 further distally into the disc space as it is inserted. To resist expulsion of implant 20 in the opposite proximal direction, endplate member 50 includes an anchoring member 68 extending distally from flange 60 and projecting outwardly from contact surface 54. Anchoring member 68 can extend from flange 60 toward leading end 56 of body portion 52 along a portion of the length of body portion 52 along longitudinal axis L. Anchoring member 68 can be centered along body portion 52 or offset from the center thereof to one side of the other. While first endplate member 30 need not be provided with an anchoring member, the provision of the same is not precluded.

Anchoring member 68 includes a longitudinally tapered shape in at least one dimension to provide at least a proximally oriented face to contact bone of the adjacent vertebral in abutting engagement to resist expulsion forces parallel to the vertebral endplate. Anchoring member 68 can include any one or combination of height, width, or cross-section that tapers in a direction from distal end 56 toward proximal end 58. In the illustrated embodiment, anchoring member 68 can include a rounded outer surface profile defined approximately by one longitudinal half of a frusto-conically shaped body extending between an inner distal end wall 70 and an outer proximal end 72 adjacent flange 60.

Anchoring member 68 is oriented so that the frusto-conical shape tapers to a reduced or lesser width and height extending from contact surface 54 adjacent proximal trailing end 58. In this configuration, anchoring member 68 provides a uniform and continuously sloped outer vertebra contacting face 74 that contacts a correspondingly shaped seat formed in the endplate of the adjacent vertebra to provide resistance to movement of the endplate member 50 in the direction of arrow 80.

When anchoring member 68 is engaged to a vertebra that is a lower or inferior vertebra, face 74 slopes caudally or inferiorly from proximal trailing end 58 toward distal leading insertion end 56. Conversely, if anchoring member 68 were engaged to a superior or upper vertebra, face 74 would slope superiorly or cephaladly from proximal trailing end 58 toward distal leading insertion end 56. In either or both arrangements, face 74 of anchoring member 68 contacts the bone surface defining the seat formed in the endplate of the adjacent vertebra to resist expulsion of the implant in the direction of arrow 80, i.e. in the direction opposite the implant insertion direction 82.

Flange 60 works in conjunction with the distal end wall 70 to provide resistance to movement of the implant in the direction of arrow 82. Accordingly the anchoring member 68 and flange 60 act in concert to resist displacement of the implant 20 when assembled, if necessary, and positioned between adjacent vertebral bodies. Anchors need not be employed to engage flange 60 to the vertebra, and flange 60 can be solid for increased strength. However, the provision of one or more anchors through flange 60 is not precluded.

The relatively short length of anchoring member 68 relative to body portion 52 between ends 56, 58 minimizes the intrusion of anchoring member 68 into the adjacent vertebra and the amount of bone removal to accommodate anchoring member 68. In one embodiment, anchoring member 68 extends along less than half the length of body portion 52 between ends 56, 58. In another embodiment, anchoring member extends along less than about three-fourths of the length of body portion 52 between ends 56, 58.

The rounded, blunt outer surface profile of face 74 of anchoring member 68 can be provided without sharp edges that cut into the vertebral body when implanted, yet anchoring member 68 provides secure engagement to resist movement of the implant 20 relative to the vertebrae. In addition, the implant 20 need not be impacted into the disc space for insertion and secure engagement of the anchoring member in the seat formed in the adjacent vertebra. Rather, the adjacent vertebra can be slightly over-distracted at least adjacent their anterior margins or other side or location through which the implant is positioned into the disc space. The distraction allows passage of distal end wall 70 of anchoring member 68 past the proximal edge of the seat and into the disc space, and then anchoring member 68 can be seated into the seat formed in the respective adjacent vertebra. The vertebrae can be re-compressed slightly to ensure an intimate fit of the endplate contacting members 30, 50 with the vertebral endplates.

Various forms for anchoring member 68 are contemplated. Outer face 74 can include surface interruptions or a non-uniform outer surface profile. Anchoring member 68 can be integrally formed at its proximal end 72 with flange 60. Proximal end 72 can be spaced from flange 60. Anchoring member 68 can include adjacent grooves or recesses extending transversely thereto or longitudinally therealong to receive bone growth. Anchoring member 68 can include pits, knurlings or other surface characteristics to receive bone ingrowth.

Figure 5:
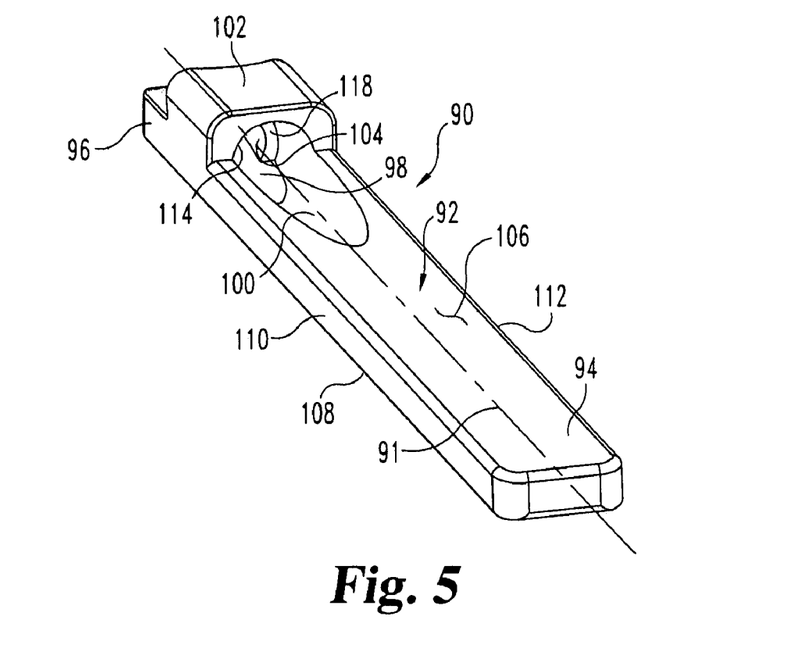
FIG. 5 is a perspective view looking distally along a trial guide instrument.
Figure 6:
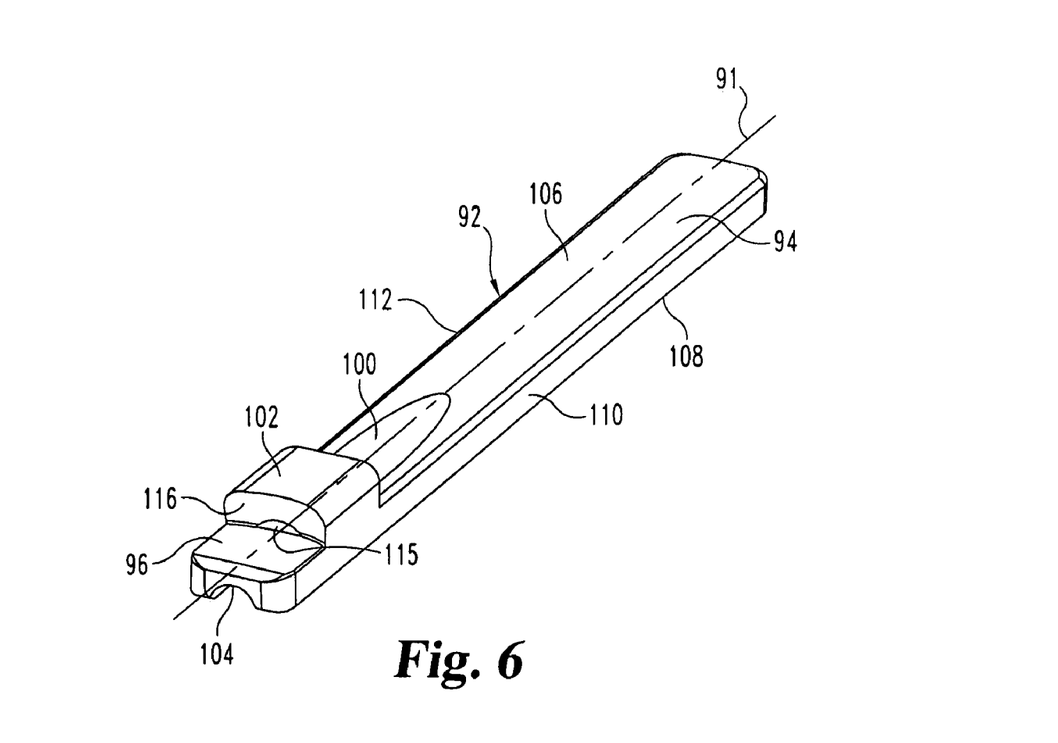
FIG. 6 is a perspective view looking proximally along the trial guide instrument of FIG. 5.

Various instruments are provided to facilitate preparation of the vertebrae to receive artificial disc implant 20 with anchoring member 68. FIGS. 5 and 6 show a trial guide instrument 90. Trial guide instrument 90 includes an elongated body 92 extending along a longitudinal axis 91 between a proximal handle portion 94 and a distal insertion portion 96. Body 92 includes a generally rectangular shape with a second side 108 opposite a first side 106. First and second sides 106, 108 are generally planar and interconnected by planar sidewalls 110, 112. A hood portion 102 extends outwardly from first side 106 of body 92 adjacent distal insertion portion 96. Hood portion 102 includes a distal surface 116 extending from first side 106 that is positionable in contact with a vertebral body when distal insertion portion 96 is located in the disc space.

Trial guide instrument 90 further includes a bore 98 extending angularly to longitudinal axis 91 between first side 106 and second side 108. Bore 98 includes a first, large diameter portion defined by a concave scalloped or recessed portion 98 extending into body 92 from first side 106. In addition, the first portion of bore 98 includes a scalloped or concavely curved surface 114 forming an inner surface of hood portion 102. Inner surface 114 forms a distal opening 115 from hood portion 102 through first side 106 along a portion of distal insertion portion 96. Bore 98 also includes a second, distal smaller diameter portion formed by a recessed or concave portion 104 along distal insertion portion 96 that extends into second side 108. The first bore portion transitions to the second bore portion at a lip 118 therebetween.

Figure 7:
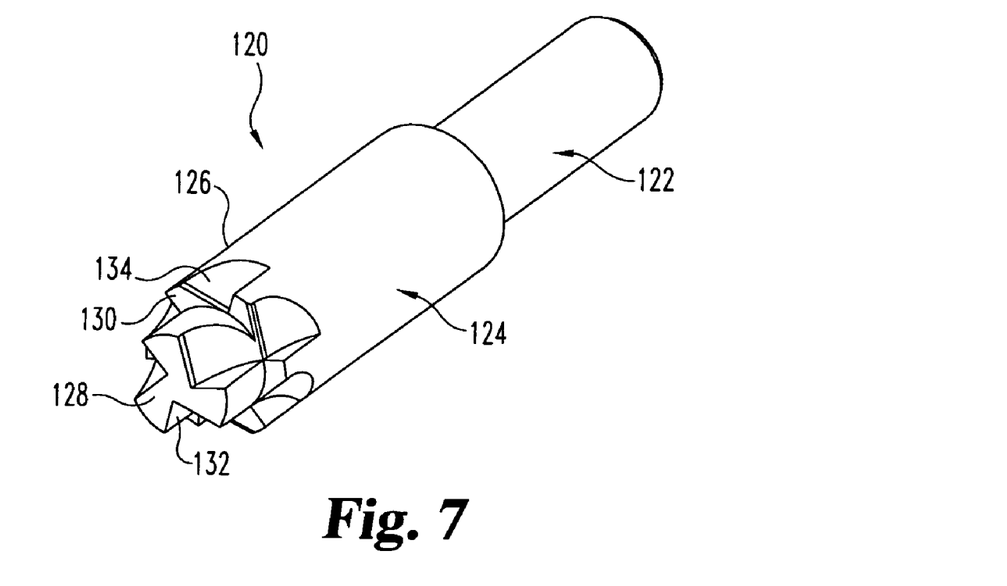
FIG. 7 is a perspective view of a reamer.
Figure 8:
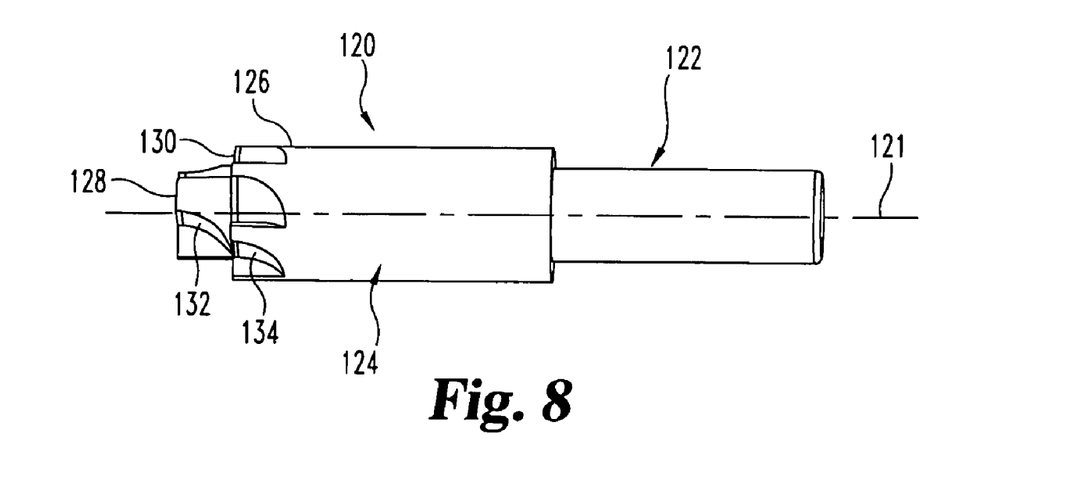
FIG. 8 is a side elevation view of the reamer of FIG. 7.

Referring now to FIGS. 7 and 8, there is shown a stepped reamer 120 useable with the trial guide instrument 90 to prepare first and second adjacent vertebrae to receive artificial disc implant 20. Stepped reamer 120 includes a proximal connecting shaft 122 that can be configured for releasable attachment to a rotary drive mechanism (not shown). Other embodiments contemplate that reamer 120 is fixably coupled with a manual or mechanical drive mechanism. Reamer 12 also includes a stepped reaming head 124 extending distally from connecting shaft 122 along longitudinal axis 121. Reaming head 124 can be configured like a reamer, drill or other suitable cutting device to remove bony tissue when operated.

Reaming head 124 includes a first cylindrical portion 126 having a first, larger diameter about axis 121 and a second cylindrical portion 128 extending distally from first cylindrical portion 126 that has a reduced, smaller diameter about axis 121. Cylindrical portion 128 includes a number of cutting flutes 132 extending thereabout at the distal end thereof, and cylindrical portion 126 has a number of cutting flutes 134 extending thereabout at the distal end thereof. An endwall 130 is provided between portions 126, 128 and extends between cutting flutes 132, 134 so that the cutting flutes defines a concentric arrangement.

Having described various elements and features associated with the artificial disc implant 20, reference will now be made to a method for implanting the artificial disc implant 20 within the intervertebral disc space D according to one form of the present invention. However, it should be understood that other implantation techniques and procedures are also contemplated, and that the following method in no way limits the scope of patent protection sought for the present invention.

Referring to FIGS. 9-13, one example of a procedure for preparing disc space D and first and second vertebrae V1, V2 to receive implant 20 with trial guide instrument 90 and stepped reamer 130 will be discussed. Initially, the portion of the spinal column to be treated is identified and accessed from an anterior approach using known surgical techniques. However, it should be understood that other surgical approaches are also contemplated including, for example, a posterior, antero-lateral, oblique, or postero-lateral approach. It should further be understood that the artificial disc implant 20 may be used to treat any region of the spinal column, including the cervical, thoracic, lumbar or sacral regions of the spine. At least a portion of the natural intervertebral disc is removed via a total or partial discectomy to provide an intervertebral disc space D for receipt of the artificial disc implant 20 between the first and second vertebrae V1, V2. The intervertebral disc space D may be distracted to a height that is substantially equal to the natural disc space height prior to disc space preparation, although such is not required.

Figure 9:
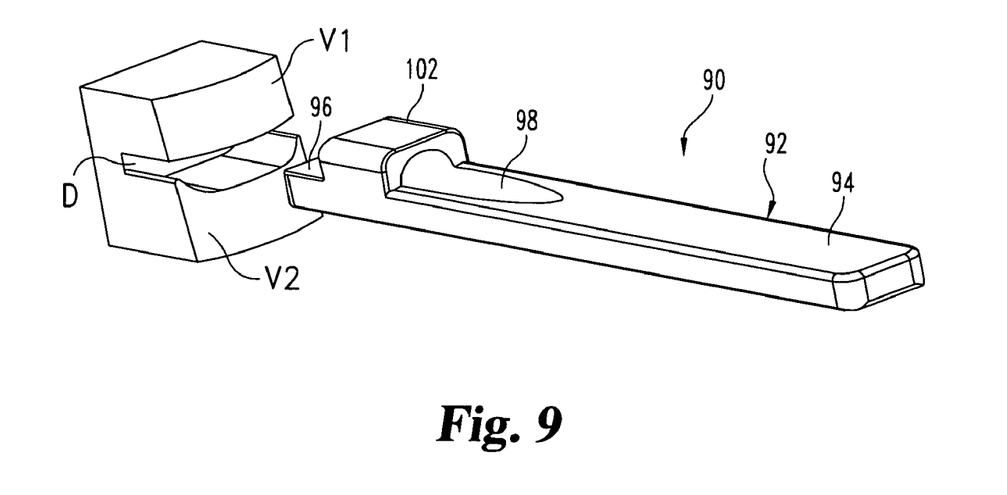
FIG. 9 is a perspective view that shows the trial guide instrument in an approach to a disc space between first and second vertebrae with the vertebrae and disc space shown diagrammatically.
Figure 10:
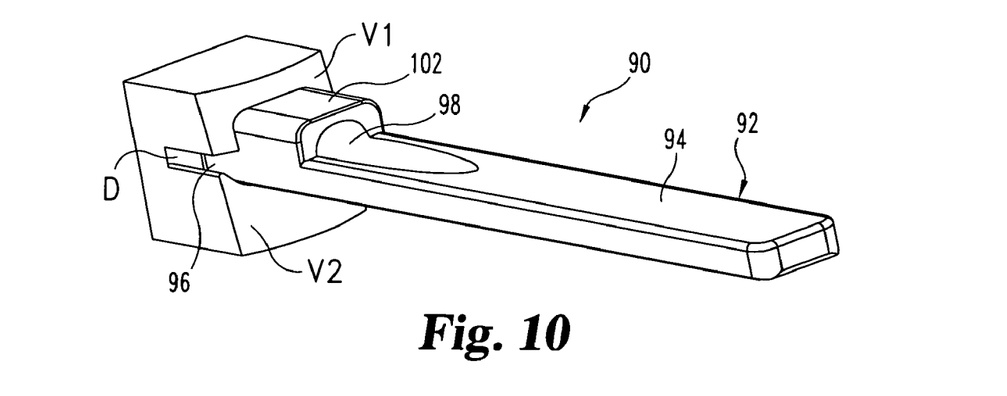
FIG. 10 is a perspective view that shows the trial guide instrument positioned in the disc space between first and second vertebrae.

In FIG. 9 trial guide instrument 90 is oriented in the access approach to disc space D between vertebra V1 and V2. Body portion 92 is oriented with distal insertion portion 96 oriented distally and handle portion 94 oriented proximally relative to the surgeon in use. In FIG. 10, distal insertion portion 96 is positioned in disc space D with distal face 116 of hood portion 102 in abutting engagement with vertebra V1. It is contemplated that a number of trial guide instruments 90 can be provided with distal insertion portions 96 having various heights between the respective upper and lower vertebral endplate contacting surfaces. The trial guide providing an intimate and desired fit within the disc space can be selected for use in guiding reamer 120. In addition, the selected trial guide instrument can provide an indication of an appropriately sized implant 20 and/or spacer member 22 for use between endplate members 30, 50 to provide the artificial disc implant 20 with an appropriate height for implantation between vertebrae V1, V2.

Figure 11:
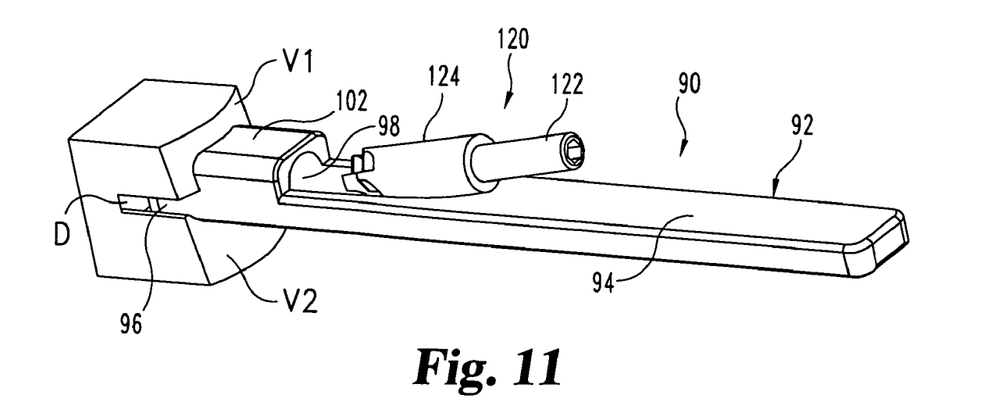
FIG. 11 is a perspective view that shows the trial guide instrument positioned in the disc space between first and second vertebrae and a reamer being positioned into the trial guide instrument toward the disc space.
Figure 12:
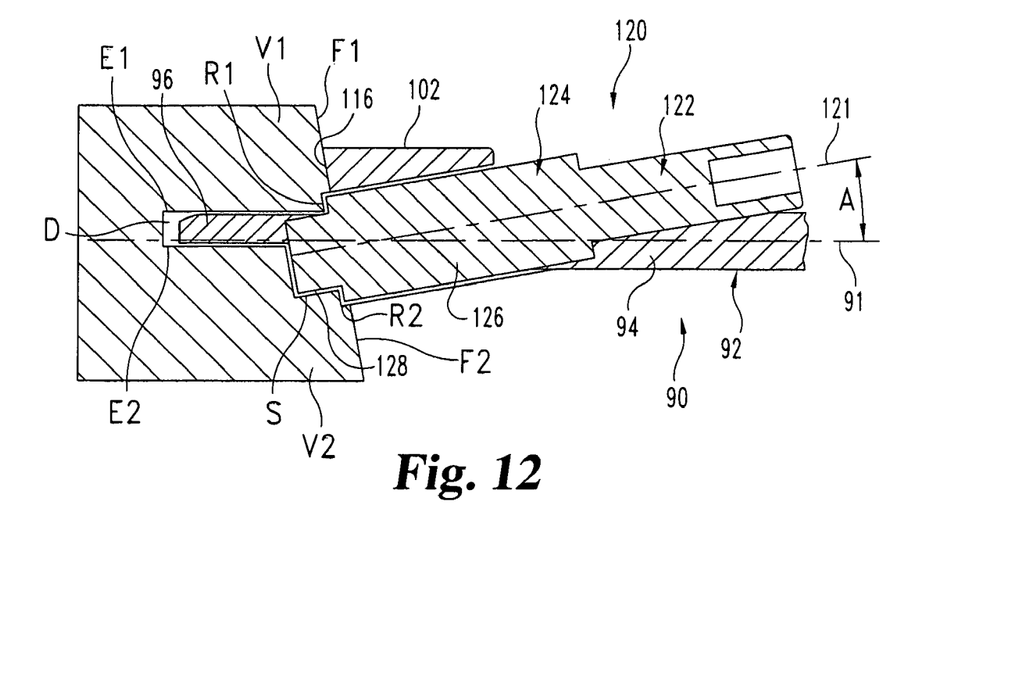
FIG. 12 is a side view that shows the trial guide instrument positioned in the disc space between first and second vertebrae and a reamer positioned into the trial guide instrument in engagement with the first and second vertebrae.

In FIG. 11 reamer 120 is positioned with reaming head 124 oriented distally and toward the proximal opening of bore 98 of trial guide instrument 90 for positioning therein. In FIG. 12 reamer 120 is positioned in bore 98 so that first cylindrical portion 126 is rotatably received in the proximal portion of bore 98, and second cylindrical portion 128 extending distally from first cylindrical portion 126 is rotatably received in the distal portion of bore 98. When positioned in bore 98, longitudinal axis 121 of reamer 120 is oriented along the same oblique angle A as bore 98 is relative to longitudinal axis 91 of trial guide instrument 90. Longitudinal axis 91 can be positioned in parallel or substantially parallel relationship with endplate E2 of vertebra V2 so that longitudinal axis 121 is also obliquely oriented to endplate E2.

Reamer 120 can be rotated to so that cutting flutes 134 of first cylindrical portion 126 remove bone material from the anterior faces F1 and F2 of vertebrae V1 and V2, respectively, forming recesses R1 and R2, respectively. Simultaneously, second cylindrical portion 128 is rotated so that cutting flutes 132 remove bone material from vertebra V2 through endplate E2 along longitudinal axis 121 and in an oblique orientation to endplate E2. Second cylindrical portion 128 can be sized so that endplate E1 of vertebra V1 remains intact as endplate material is removed from vertebra V2.

Figure 13:
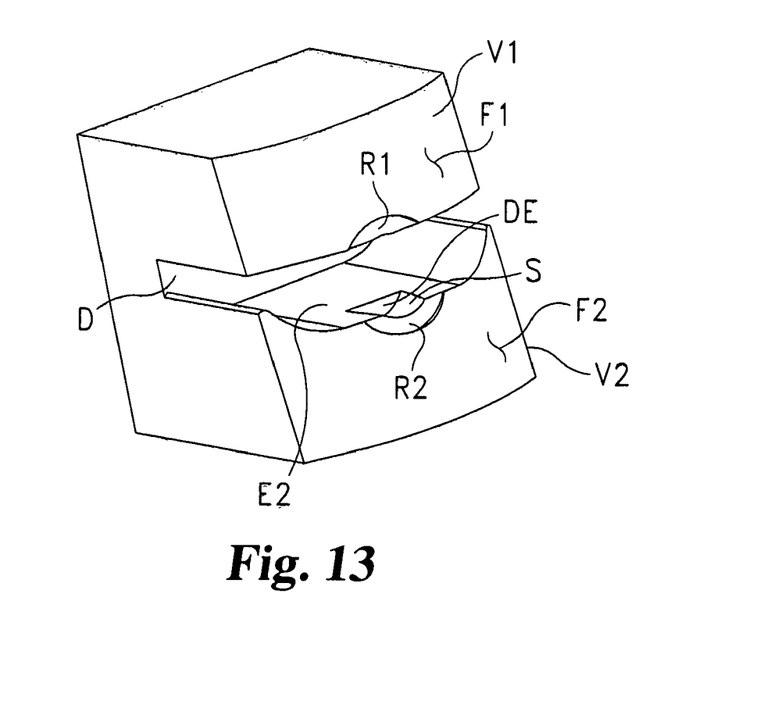
FIG. 13 is an elevation view showing the first and second vertebrae prepared with the trial guide instrument and reamer according to FIGS. 9-12.

In FIG. 13 there is shown diagrammatically the vertebral bodies V1 and V2 looking at the anterior faces thereof and as prepared in accordance with the use of the instrument assembly comprising the trial guide instrument 90 and stepped reamer 120. Vertebral body V1 includes recess R1 in anterior face F1. Recess R1 includes a semi-circular shape and depth that can correspond to the length of opening 115 of bore 98 along distal insertion portion 96. Second vertebra V2 includes a similarly shaped and aligned recess R2 in anterior face F2 having a depth that approximates the depth of recess R1. The depth of the respective recesses R1 and R2 can vary across their respective widths as a result of the curvature of the anterior faces F1, F2 about the respective vertebral bodies. The depth of recess R1 and R2 along the central axis of the spinal column can be constant, or can vary as a result of non-orthogonal orientations between faces F1 and F2 and longitudinal axis 121 since reamer 120 is advanced along axis 121 and head 124 is rotated about axis 121.

In addition to recesses R1 and R2, second cylindrical portion 128 of reamer head 124 forms seat S in endplate E2 of vertebra V2. Seat S includes a bottom surface concavely curved about longitudinal axis 121 and extending linearly from recess R2 to a distal end surface DE at a distal end of seat S. The depth of seat S at distal end surface DE is greater than its depth adjacent recess R2. In addition, the width of seat S at distal end surface DE is greater than the width of seat S at recess R2. In the illustrated embodiment, seat S has a shape that corresponds substantially to the shape of a longitudinal half of a frusto-conical form. In areas of vertebrae V1, V2 where bone is not removed, the cortical rim/apophyseal ring region of the vertebral endplates remaining substantially intact.

Other embodiments contemplate other techniques for reaming the intervertebral space to prepare the vertebrae to receive artificial disc implant 20. For example, the removal of bone material from the bony portions aligned with the distal and proximal portions of bore 98 can be done separately and sequentially with separate reamers of appropriately sized reaming heads. Other embodiments contemplated non-rotary removal of bone from vertebra V2. Examples include longitudinally moving cutting members, gougers, scrapers, chisels, impulsive-type instruments, and reciprocating type instruments, for example, that can remove bone along an axis obliquely oriented to endplate E2. It is also contemplated that seat S could be formed by freehand techniques and instruments.

Figure 14:
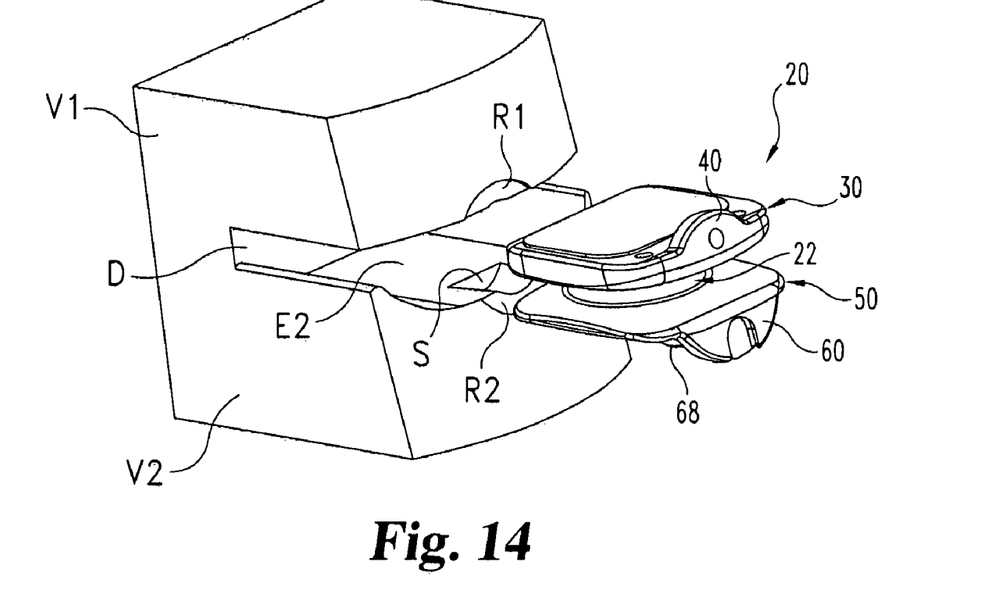
FIG. 14 is a perspective view showing the artificial disc implant of FIG. 1 in an approach for positioning into the disc space between the prepared first and second vertebrae of FIG. 13.
Figure 17:
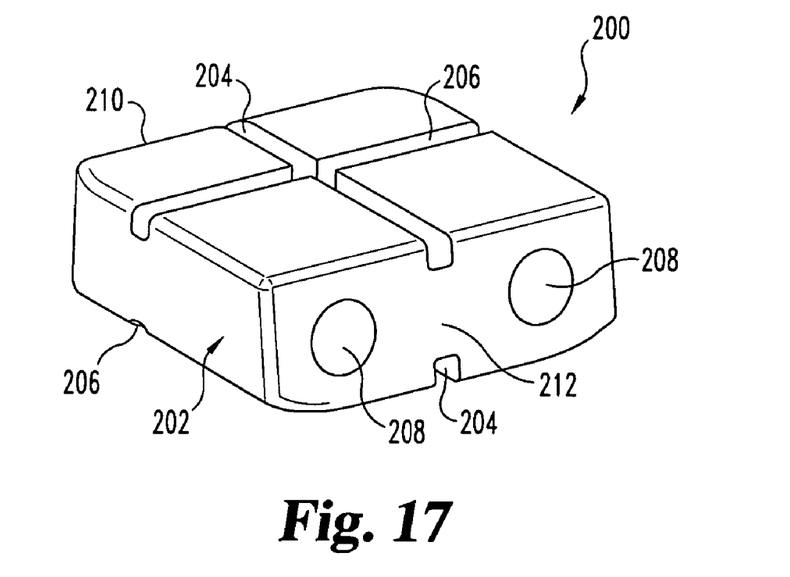
FIG. 17 is a perspective view of a trial block positionable in the disc space between the first and second vertebra.

In FIG. 14 there is shown artificial disc implant 20 in the approach to the prepared intervertebral space with flanges 40, 60 oriented proximally and anchoring member 68 oriented toward vertebra V2. Vertebra V1 and V2 can be distracted slightly and in particularly at the anterior margins of the endplates adjacent anterior faces F1 and F2 to allow passage of distal end wall 70 past the anterior edge of seat S. Prior to insertion of artificial disc implant 20 into disc space D, a trial block 200, such as shown in FIG. 17, can be positioned in disc space D to provide an indication of the fit of implant 20.

Various trial blocks 200 of various height and/or other lateral dimensions can be provided so that the implant 20 of appropriate size can be selected prior to insertion. In the illustrated embodiment, trial block 200 includes a rectangular body with longitudinal grooves 204 in its upper and lower surfaces and lateral grooves 206 in its upper and lower surfaces. When viewed on X-rays or other imaging platform and when trial block 200 is inserted in the disc space, longitudinal grooves 204 can provide a visual indication of the location of trial block 200 in the disc space relative to the spinal midline, while lateral grooves 206 can provide an indication of the location in the anterior-posterior direction of the midline of spacer member 22 relative to the vertebral endplates. Holes 208 in trailing end 212 can receive a tool to facilitate insertion and withdrawal of body 202 from the disc space. The leading end 210 can be tapered to facilitate insertion between the vertebrae, and trailing end 212 can be contoured or tapered to conform to the profile of the anterior faces of vertebrae V1, V2.

Figure 15:
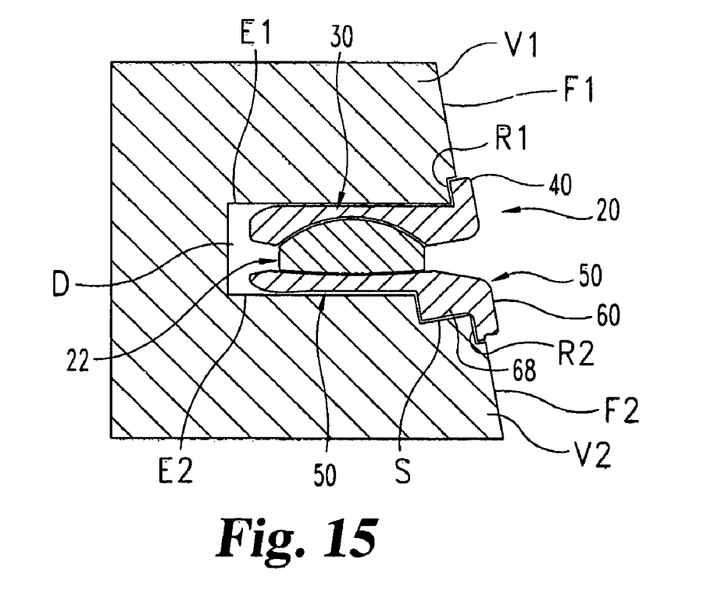
FIG. 15 is a side, sectional view showing the artificial disc implant of FIG. 1 positioned into the disc space between the prepared first and second vertebrae of FIG. 13.
Figure 16:
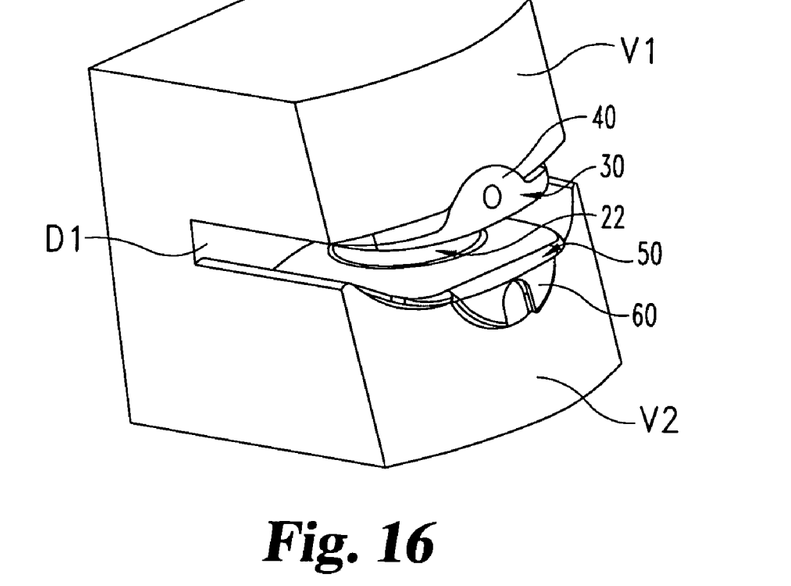
FIG. 16 is a perspective view showing the artificial disc implant of FIG. 1 positioned into the disc space between the prepared first and second vertebra of FIG. 13.

FIGS. 15 and 16 provide views of artificial disc implant 20 located in disc space D and with anchoring member 68 seated in seat S to resist movement of implant 20 relative to vertebrae V1 and V2. The proximally tapering shape of anchoring member 68 can provide a proximally oriented face engaging vertebra V2 in seat S that resists expulsion forces of the implant that are generated parallel to the endplates E1, E2.

In the illustrated embodiment, anchoring member 68 and seat S have a longitudinal portion that defines a rounded, concavely curved depression in vertebra V2 that radially tapers from the distal end to the proximal end. However, it should be understood that other shapes and configurations of the anchoring member 68 and seat S are also contemplated including, for example, linearly and non-linearly longitudinally tapering shapes, uni-dimensionally tapering shapes, pyramidal shapes, or other non circular cross-sectional shapes that could be formed by an appropriate cutting instrument.

Anchoring member 68 can act, in conjunction of the engagement of first endplate member 30 with spacer member 22 and the engagement of spacer member 22 with second endplate member 50, to reduce the likelihood of migration and possible expulsion of the artificial disc implant 20 from the intervertebral disc space D. Although it is contemplated that the artificial disc implant 20 may be used without any other means of fixation, it should be understood that supplemental external intravertebral fixation elements and/or stabilization techniques may be used if excessive residual instability is encountered following insertion of the artificial disc implant 20 within the intervertebral disc space D. Moreover, first and second endplate members 30, 50 are positioned against or adjacent the opposing surfaces of the first and second vertebrae V1, V2 after distraction of vertebrae V1, V2. Compression from the weight of the spinal column above the upper vertebra can provide and/or maintain positive contact between the endplates and the first and second endplate members 30, 50. External compression forces may also be provided after implantation of artificial disc implant 20 to provide or enhance contact between first and second endplate members 30, 50 and the adjacent endplates of vertebrae V1 and V2. In instances where the annulus of the intervertebral disc remains at least partially intact, initial distraction prior to implantation of artificial disc implant 20 tightens and possibly stretches the disc annulus, thereby providing additional stabilization of the first and second vertebrae V1, V2.

As should be appreciated, if removal of the artificial disc implant 20 from the intervertebral disc space D is required due to non-optimal placement or for other reasons, the vertebrae can be distracted sufficiently at least adjacent their anterior margins a sufficient distance to allow passage of anchoring member 68 by the proximal edge of seat S adjacent recess R2 of vertebra V2. Of course, any screws or anchoring members engaging artificial disc implant 20 to vertebra V1 and V2 should also be removed before withdrawal of the implant from the disc space.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An artificial disc for implantation within an intervertebral disc space between first and second vertebrae, comprising:
    a first endplate member having an outer surface for contacting an endplate of an adjacent first vertebra and an opposite inner surface, said first endplate member including a body portion extending between a distal leading end and a proximal trailing end;
    a second endplate member having an outer surface for contacting an endplate of an adjacent second vertebra and an opposite inner surface, said second endplate member including a body portion extending between a distal leading end and a proximal trailing end;
    a spacer member extending between and engaging said first and second endplate members in movable relation to one another; and
    an anchoring member extending from said outer surface of at least one of said first and second endplate members, said anchoring member extending distally from a first end adjacent said proximal trailing end to a distal end wall spaced distally from said first end of said anchoring member and located proximally of said distal leading end of said endplate member, said distal end wall of said anchoring member defining a height extending from said outer surface of said endplate member that is greater than a height of said first end extending from said outer surface of said endplate member, said distal end wall of said anchoring member including a first width that is greater than a second width of said anchoring member at said first end, wherein said anchoring member tapers from said height at said distal end wall to said height of said first end and said anchoring member tapers from said first width to said second width.

2. The artificial disc of claim 1, wherein said spacer member is compressible and elastic.

3. The artificial disc of claim 1, wherein said spacer member includes at least one end positionable in contact with said first end plate member, said at least one end including a convexly curved dome shape.

4. The artificial disc of claim 3, wherein said first endplate member includes a concavely curved recess in said inner surface for receiving said at least one end of said spacer member.

5. The artificial disc of claim 1, wherein said spacer member includes a cylindrical body extending between said inner surfaces.

6. The artificial disc of claim 1, wherein said proximal trailing end of said body portion of said first endplate member includes a flange extending therefrom in a direction away from said second endplate member.

7. The artificial disc of claim 6, wherein said flange defines a dome shape projecting from said outer surface.

8. The artificial disc of claim 7, wherein said flange includes a bore for receiving a bone anchor to engage said first endplate member to the first vertebra.

9. The artificial disc of claim 6, wherein said second endplate member includes a flange extending from said proximal trailing end of said body portion thereof in a direction away from said first endplate member, said flange including a groove formed in a side thereof facing away from said distal leading end.

10. The artificial disc of claim 9, wherein said first end of said anchoring member is integral with and extends from said flange of said second endplate member.

11. The artificial disc of claim 1, wherein said anchoring member includes a length along said outer surface between said first end and said distal end wall that is less than one half the length of said body portion of said one of said first and second endplate members between said distal leading end and said proximal trailing end.

12. The artificial disc of claim 1, wherein said anchoring member is centered on said outer surface of said one of said first and second endplate members.

13. The artificial disc of claim 1, wherein said anchoring member includes an outer face between said first end and said distal end wall that defines a longitudinal half of a frusto-conical shape positioned on said endplate contacting surface so that a convexly rounded side of said half of said frusto-conical shape extends from said endplate contacting surface in a direction opposite said first endplate member and a side of said half of said frusto-conical shape that is opposite said convexly rounded side is positioned facing said endplate contacting surface of said second endplate member, wherein said half of said frusto-conical shape further includes opposite ends corresponding to respective ones of said first end and said distal end wall of said anchoring member, said ends extending between and connecting said convexly rounded side of said anchoring member to said endplate contacting surface of said second endplate member.

14. The artificial disc of claim 1, wherein said anchoring member defines an outer surface with a rounded, blunt profile that tapers in height and width from said distal end wall to said first end of said anchoring member.

15. The artificial disc of claim 1, wherein said second endplate member includes a flange extending from a proximal trailing end thereof in a direction away from said first endplate member and said anchoring member includes a first end that is connected directly to and extends from said flange of said second endplate member.

16. An artificial disc for implantation within an intervertebral disc space between first and second vertebrae, comprising:
first and second endplate members coupled in movable relation to one another, wherein said first and second endplate members are sized and shaped for positioning in the intervertebral disc space and for movably supporting the adjacent vertebrae, and further comprising an anchoring member extending from an endplate contacting surface of said second endplate member in a direction opposite said first endplate member, said anchoring member including an outer surface defining a longitudinal half of a frusto-conical shape positioned on said endplate contacting surface so that a convexly rounded side of said half of said frusto-conical shape extends from said endplate contacting surface of said second endplate member in said direction opposite said first endplate member and a side of said half of said frusto-conical shape that is opposite said convexly rounded side is positioned facing said endplate contacting surface of said second end late member, wherein said half of said frusto-conical shape further includes opposite ends extending between and connecting said convexly rounded side of said anchoring member to said endplate contacting surface of said second endplate member, wherein said end of said half of said frusto-conical shape closest to a distal leading end of said second endplate member has a greater width than said end of said half of said frusto-conical shape closest to a proximal trailing end of said second endplate member.

17. The artificial disc of claim 16, wherein said first and second endplate members each include a distal leading end and a proximal trailing end and said anchoring member extends from a location adjacent said proximal trailing end along said endplate contacting surface toward said distal leading end.

18. The artificial disc of claim 16, further comprising a spacer member between said first and second endplate members coupling said first and second endplate members in movable relation to one another.

19. The artificial disc of claim 16, wherein said second endplate member includes a flange extending from a proximal trailing end thereof in a direction away from said first endplate member and said anchoring member includes a first end that is connected directly to and extends from said flange of said second endplate member.

20. An artificial disc for implantation within an intervertebral disc space between first and second vertebrae, comprising:
first and second endplate members coupled in movable relation to one another, wherein said first and second endplate members are sized and shaped for positioning in the intervertebral disc space and for movably supporting the adjacent vertebrae, wherein said first and second endplate members each include a distal leading end and a proximal trailing end, and further comprising an anchoring member extending from an endplate contacting surface of said second endplate member in a direction opposite said first endplate member, said anchoring member extending from a first end of said anchoring member adjacent said proximal trailing end to a second end of said anchoring member spaced distally from said first end so that said second end is located more adjacent to said distal leading end of said second endplate member than said first end of said anchoring member and so that said first end of said anchoring member is located more adjacent said proximal trailing end of said second endplate member than said second end of said anchoring member, said anchoring member including a length between said first and second ends that is less than about three-fourths of a length of said second endplate member between said proximal trailing end and said distal leading end thereof, wherein said anchoring member defines an outer surface with a rounded, blunt profile that tapers in height and width so that said height and said width each decrease from said second end to said first end of said anchoring member.

21. The artificial disc of claim 20, wherein said anchoring member includes an outer surface between said first end and said second end that defines a longitudinal half of a frusto-conical shape positioned on said endplate contacting surface of said second endplate member so that a convexly rounded side of said half of said frusto-conical shape extends from said endplate contacting surface of said second endplate member in a direction opposite said first endplate member and a side of said half of said frusto-conical shape that is opposite said convexly rounded side is positioned facing said endplate contacting surface of said second endplate member, wherein said half of said frusto-conical shape further includes opposite ends corresponding to respective ones of said first end and said second end of said anchoring member, said ends extending between and connecting said convexly rounded side of said anchoring member to said endplate contacting surface of said second endplate member.

22. The artificial disc of claim 20, wherein said length between said first and second ends of said anchoring member that is less than half the length of said second endplate member between said proximal trailing end and said distal leading end thereof.

23. The artificial disc of claim 20, further comprising a spacer member between said first and second endplate members coupling said first and second endplate members in movable relation to one another.

24. The artificial disc of claim 20, wherein said second endplate member includes a flange extending from said proximal trailing end away from said first endplate member and said first end of said anchoring member is connected directly to said flange and said anchoring member extends distally therefrom.

25. An artificial disc for implantation within an intervertebral disc space between first and second vertebrae, comprising:
first and second endplate members coupled in movable relation to one another, wherein said first and second endplate members are sized and shaped for positioning in the intervertebral disc space and for movably supporting the adjacent vertebrae, wherein said first and second endplate members each include a distal leading end and a proximal trailing end, and further comprising an anchoring member extending from an endplate contacting surface of said second endplate member in a direction opposite said first endplate member, said anchoring member including a length extending from a first end of said anchoring member adjacent said proximal trailing end to a second end of said anchoring member spaced distally from said first end so that said second end of said anchoring member is located more adjacent said distal leading end of said second endplate member than said first end of said anchoring member and so that said first end of said anchoring member is located more adjacent said proximal trailing end of said second endplate member than said second end of said anchoring member, said anchoring member including a first width at said first end and that is less than a second width at said second end.

26. The artificial disc of claim 25, wherein said anchoring member tapers from said second width to said first width.

27. The artificial disc of claim 26, wherein said anchoring member includes a first height at said first end thereof and a second height at said second end thereof, said first and second heights each extending from said endplate contacting surface and said second height is greater than said first height, wherein said anchoring member tapers from said second height to said first height.

28. The artificial disc of claim 27, wherein said length between said first and second ends of said anchoring member is less than half a length of said second endplate member between said proximal trailing end and said distal leading end thereof.

29. The artificial disc of claim 28, wherein said anchoring member includes an outer surface between said first end and said second end that defines a longitudinal half of a frusto-conical shape positioned on said endplate contacting surface of said second endplate member so that a convexly rounded side of said half of said frusto-conical shape extends from said endplate contacting surface of said second endplate member in a direction opposite said first endplate member and a side of said half of said frusto-conical shape that is opposite said convexly rounded side is positioned facing said endplate contacting surface of said second endplate member, wherein said half of said frusto-conical shape further includes opposite ends corresponding to respective ones of said first end and said second end of said anchoring member, said ends extending between and connecting said convex rounded side of said anchoring member to said endplate contacting surface of said second endplate member.

30. The artificial disc implant of claim 25, wherein said anchoring member defines an outer surface with a rounded, blunt profile that tapers in height and width from said second end to said first end of said anchoring member.

31. The artificial disc of claim 25, wherein said second endplate member includes a flange extending from said proximal trailing end thereof in a direction away from said first endplate member and said first end of said anchoring member is connected directly to and extends from said flange of said second endplate member.

32. The artificial disc of claim 31, wherein said flange includes a solid groove formed in a side thereof facing away from said distal leading end.

\* \* \* \* \*